(12) United States Patent  
Matsuyama et al.

(10) Patent No.: US 7,730,108 B2
(45) Date of Patent: Jun. 1, 2010

(54) INFORMATION PROCESSING APPARATUS AND METHOD, AND PROGRAM

(75) Inventors: Shinako Matsuyama, Tokyo (JP); Yu Hamada, Tokyo (JP); Tetsuya Shiraishi, Tokyo (JP)

(73) Assignee: Sony Corporation, Tokyo (JP)

( * ) Notice: Subject to any disclaimer, the term of this patent is extended or adjusted under 35 U.S.C. 154(b) by 360 days.

(21) Appl. No.: 11/948,905

(22) Filed: Nov. 30, 2007

(65) Prior Publication Data

US 2008/0154964 A1 Jun. 26, 2008

(30) Foreign Application Priority Data

Dec. 20, 2006 (JP) ............................. P2006-342874

(51) Int. Cl.
*G06F 17/30* (2006.01)
(52) U.S. Cl. ...................... 707/802; 707/797; 707/956
(58) Field of Classification Search ................... 707/100
See application file for complete search history.

(56) References Cited

U.S. PATENT DOCUMENTS 5,598,350 A * 1/1997 Kawanishi et al. ............ 702/20
2004/0204925 A1* 10/2004 Alon et al. ..................... 703/2

FOREIGN PATENT DOCUMENTS

JP 2002-091991 3/2002

OTHER PUBLICATIONS

R. Milo, et al., "Superfamilies of Evolved and Designed Networks", Science, 303, pp. 1538-1542 (2004).
R. J. Prill et al., "Dynamic Properties of Network Motifs Contribute to Biological Network Organization", PLOS Biology, Nov. 2005, vol. 3, Issue 1, pp. 1881-1892.
S. Itzkovitz et al., "Subgraphs in Random Networks", Physical Review E 68, 026127, The American Physical Society, Aug. 25, 2003, pp. 68-026127-1 to 68-026127-8.
M. Kuramochi et al., "Frequent Subgraph Discovery", IEEE International Conference on Data Mining, 2001, pp. 1-14.
N. Kashtan et al., "mfinder Tool Guide", Department of Molecular Cell Biology and Computer Science & Applied Mathematics, Weizmann Institute of Science, version 1.2, May 2005, http://www.weizmann.ac.il/mcb/UriAlon/.

* cited by examiner

*Primary Examiner*—Cheryl Lewis
(74) *Attorney, Agent, or Firm*—Finnegan, Henderson, Farabow, Garrett & Dunner, L.L.P.

(57) ABSTRACT

Disclosed herein is an apparatus for processing information about a network including a plurality of nodes, wherein m attributes (m represents an integer of 2 or more) assignable to each of the nodes are defined depending on the relationship to another node which can be connected to the each of the nodes, the apparatus including: identifier generating means for converting attributes assigned to each of n nodes (n represents an integer of 3 or more) per relationship to the other node connected thereto into numerical values with respect to motifs extracted from the network as predetermined patterns of the connected relationship of the n nodes, and generating identifiers identifying the motifs using the numerical values.

7 Claims, 13 Drawing Sheets

FIG.4

| in_num | out_num | LINK NUMERICAL VALUE (=in_num*3+out_num) |
|---|---|---|
| 0 | 0 | 0 |
| 0 | 1(N) | 1 |
| 0 | 2(P) | 2 |
| 1(N) | 0 | 3 |
| 1(N) | 1(N) | 4 |
| 1(N) | 2(P) | 5 |
| 2(P) | 0 | 6 |
| 2(P) | 1(N) | 7 |
| 2(P) | 2(P) | 8 |

FIG.5

Motif FILE

| THREE NODE NAMES | | | motif ID (original) | motif ID (unique) | NODE POSITIONAL RELATIONSHIP INFORMATION | | |
|---|---|---|---|---|---|---|---|
| v1 | v2 | v3 | | | v1_node_num | v2_node_num | v3_node_num |
| D | E | F | 262626 | 262626 | 1 | 2 | 3 |
| B | A | C | 484758 | 474858 | 2 | 1 | 3 |
| ... | ... | ... | ... | ... | ... | ... | ... |

FIG. 6

| Motif ID FILE ||
|---|---|
| motif ID (unique) | NUMBER OF OCCURRENCES |
| 262626 | 7894 |
| 454858 | 8231 |
| ⋮ | ⋮ |

FIG.10

| GRAPH PATTERN | NUMBER OF OCCURRENCES (OCCURRENCE PERCENTAGE) | Motif ID (unique) | MAJOR INTERMEDIARY NODES |
|---|---|---|---|

| Graph Pattern | Motif ID (unique) | Number of Occurrences (Occurrence Percentage) | Major Intermediary Nodes |
|---|---|---|---|
| (triangle w/ circled node) | 222666 | 99% | JUN<br>SP1<br>TP53<br>SP3<br>Transcription factor |
| | 162236 | 0.2% | |
| | 122366 | 0.5% | |
| | 121336 | 0% | |
| | 122636 | 0.2% | |
| | 121633 | 0% | |
| | 112336 | 0% | |
| | 111333 | 0% | |

INFORMATION PROCESSING APPARATUS AND METHOD, AND PROGRAM

CROSS REFERENCES TO RELATED APPLICATIONS

The present invention contains subject matter related to Japanese Patent Application JP 2006-342874 filed in the Japan Patent Office on Dec. 20, 2006, the entire contents of which being incorporated herein by reference.

BACKGROUND OF THE INVENTION

1. Field of the Invention

The present invention relates to an information processing apparatus and method, and a program, and more particularly to an information processing apparatus and method, and a program for analyzing a network in a short time through an easy process.

2. Description of the Related Art

In recent years, efforts have been made to research and develop the technology for analyzing a network of interconnected protein molecules (hereinafter referred to as "protein network"). For example, R. Milo, S. Itzkovitz, N. Kashtan, R. Levitt, S. Shen-Orr, I. Ayzenshtat, M. Sheffer, and U. Alon, "Superfamilies of designed and evolved networks", Science, 303: 1538-42 (2004) (hereinafter referred to as Non-Patent Document 1) discloses the technology for measuring the frequency of occurrences of patterns (hereinafter referred to as "motifs" or "Motifs") of three interconnected nodes, each representing a protein, in a protein network.

According to the related art including the Non-Patent Document 1, a large expenditure of time and labor is taken to analyze a protein network because there are many types of proteins to be handled as nodes.

For example, it is important to extract major partial structures from a protein network in knowing the causal association of functions of proteins and also in contributing to estimating carcinogenic processes in cancer research and finding cancer treatment points. It is also of importance to investigate the roles of nodes (to act on other nodes) and determine what types of proteins exist as nodes having those roles, from the extracted major partial structures.

If a protein network is analyzed according to the related art including the Non-Patent Document 1, then a large expenditure of time and labor is taken simply to detect the frequency of occurrences of motifs. Furthermore, a subsequent process of extracting motifs that occur highly frequently as major structures and of investigating the roles of nodes (to act on other nodes) in those motifs and determining what types of proteins exist as nodes having those roles is also in need of a huge expenditure of time and labor.

The problems described above with respect to the analysis of a protein network are also applicable to the analysis of other networks made up of a number of nodes.

According to an embodiment of the present invention, it is desirable to provide an information processing apparatus and method, and a program for analyzing a network in a short time through an easy process.

SUMMARY OF THE INVENTION

It is desirable to provide an information processing apparatus and method, and a program for analyzing a network in a short time through an easy process.

According to an embodiment of the present invention, there is provided an apparatus for processing information about a network including a plurality of nodes, wherein m attributes (m represents an integer of 2 or more) assignable to each of the nodes are defined depending on the relationship to another node which can be connected to the each of the nodes, the apparatus including identifier generating means for converting attributes assigned to each of n nodes (n represents an integer of 3 or more) per relationship to the other node connected thereto into numerical values with respect to motifs extracted from the network as predetermined patterns of the connected relationship of the n nodes, and generating identifiers identifying the motifs using the numerical values.

The apparatus further includes analyzing means for determining at least one of the motifs included in the network as an object to be analyzed based on the identifier generated by the identifier generating means, and performing a predetermined analyzing process on the object to be analyzed.

The analyzing means calculates the number of occurrences in the network of a corresponding motif with respect to each of the identifiers generated by the identifier generating means according to the analyzing process.

Then apparatus further includes presenting means for presenting the number of occurrences and information about the corresponding motif with respect to each of the identifiers generated by the identifier generating means.

The presenting means further presents information about a predetermined one of the n nodes included in the corresponding motif with respect to the each of the identifiers generated by the identifier generating means.

The analyzing means retrieves one or more identifiers corresponding to one or more motifs including a predetermined node from the identifiers generated by the identifier generating means, and the presenting means further presents information about each of the one or more motifs corresponding to the one or more identifiers retrieved by the analyzing means.

A method of processing information about a network and a program for processing information about a network according to another embodiment of the present invention are a method and a program, respectively, for the above apparatus for processing information.

According to the above apparatus, method, and program, m attributes (m represents an integer of 2 or more) assignable to each of the nodes are defined depending on the relationship to another node which can be connected to the each of the nodes. Attributes assigned to each of n nodes (n represents an integer of 3 or more) per relationship to the other node connected thereto are converted into numerical values with respect to motifs extracted from the network as predetermined patterns of the connected relationship of the n nodes, and identifiers identifying the motifs are generated using the numerical values.

According to an embodiment of the present invention, a network can be analyzed. Particularly, a network can be analyzed in a short time through an easy process.

Embodiments of the present invention will be described below. Components called for in claims and specific components described in the embodiments below are related to each other as described below. The description of the relation between those claimed components and specific components serves to confirm that the specific components that support the invention described in the claims are described in the embodiments. Just because there are specific components described in the embodiments, but not described to refer to claimed components do not necessarily mean that those specific components do not correspond to claimed components. Conversely, just because there are specific components described to refer to claimed components does not necessarily mean that those specific components do not correspond to other components than claimed components.

The description of the relation between those claimed components and specific components does not serve to confirm that all of the specific components described in the embodiment are called for in the claims. Stated otherwise, the description of the relation between those claimed components and specific components does not deny the existence of inventions covering specific components that are described in the embodiment, but not called for in the claims, i.e., the existence of inventions which may be filed in divisional applications and/or added by way of amendments in the future.

According to an embodiment of the present invention, there is provided an apparatus (e.g., an information processing apparatus 11 shown in FIG. 1) for processing information about a network including a plurality of nodes, wherein m attributes (e.g., "P" and "N" to be described later) (m represents an integer of 2 or more) assignable to each of the nodes are defined depending on the relationship to another node which can be connected to the each of the nodes, the apparatus including:

identifier generating means (e.g., a processor 31 shown in FIG. 1) for converting attributes assigned to each of n nodes (n represents an integer of 3 or more) per relationship to the other node connected thereto into numerical values with respect to motifs (e.g., motifs formed with three black dots as nodes as shown in FIG. 8) extracted from the network as predetermined patterns of the connected relationship of the n nodes, and generating identifiers (e.g., MotifID(unique) shown in FIG. 5, specifically MotifID(unique)="162236" shown in FIG. 8) identifying the motifs using the numerical values (e.g., node link numerical values v1_node_num, v2_node_num, v3_node_num to be described later, specifically, the numerical values displayed near the nodes shown in FIG. 8, i.e., 16 (=v1_node_num, 36 (=v2_node_num), 22 (=v3_node_num) shown in FIG. 8).

The apparatus further includes:

analyzing means (e.g., a data analyzer 22 shown in FIG. 1) for determining at least one of the motifs included in the network as an object to be analyzed based on the identifier generated by the identifier generating means, and performing a predetermined analyzing process on the object to be analyzed.

The analyzing means calculates the number of occurrences in the network of a corresponding motif with respect to each of the identifiers generated by the identifier generating means according to the analyzing process (e.g., see step S5 shown in FIG. 3).

The apparatus further includes:

presenting means (e.g., a display 42 shown in FIG. 1 for displaying an image including "CORRESPONDING NUMBER OF Motifs: 5405" representing the number of occurrences and a graph pattern which is an example of information about the corresponding motif, as shown in FIG. 8) for presenting the number of occurrences and information about the corresponding motif with respect to each of the identifiers generated by the identifier generating means.

The presenting means further presents information (e.g., "a node group at the position of the node" referred to in step S43 shown in FIG. 9 and step S52 shown FIG. 11) about a predetermined one of the n nodes included in the corresponding motif with respect to the each of the identifiers generated by the identifier generating means.

The analyzing means retrieves one or more identifiers corresponding to one or more motifs including a predetermined node from the identifiers generated by the identifier generating means, and the presenting means further presents information about each of the one or more motifs corresponding to the one or more identifiers retrieved by the analyzing means (e.g., see FIGS. 12 and 13).

According to another embodiment of the present invention, there is provided a method of processing information in an apparatus (e.g., an information processing apparatus 11 shown in FIG. 1) for processing information about a network including a plurality of nodes, wherein m attributes (m represents an integer of 2 or more) assignable to each of the nodes are defined depending on the relationship to another node which can be connected to the each of the nodes, the method including the steps (e.g., step S3 shown in FIG. 3) of:

converting attributes assigned to each of n nodes (n represents an integer of 3 or more) per relationship to the other node connected thereto into numerical values with respect to motifs extracted from the network as predetermined patterns of the connected relationship of the n nodes; and generating identifiers identifying the motifs using the numerical values.

A program according to still another embodiment of the present invention is a program corresponding to the method of processing information according to the above embodiment of the present invention, and is executed by a computer constructed as shown in FIG. 14, for example.

The above and other features and advantages of the present invention will become apparent from the following description when taken in conjunction with the accompanying drawings which illustrate preferred embodiments of the present invention by way of example.

BRIEF DESCRIPTION OF THE DRAWINGS

FIG. 4 is a diagram illustrative of a portion of a process of calculating MotifID;

FIG. 5 is a diagram showing an example of the structure of a Motif file;

FIG. 6 is a diagram showing an example of the structure of a Motif ID file;

FIG. 10 is a diagram showing an example of the result of the motif details displaying process shown in FIG. 9;

DETAILED DESCRIPTION OF THE PREFERRED EMBODIMENTS

Figure 1:
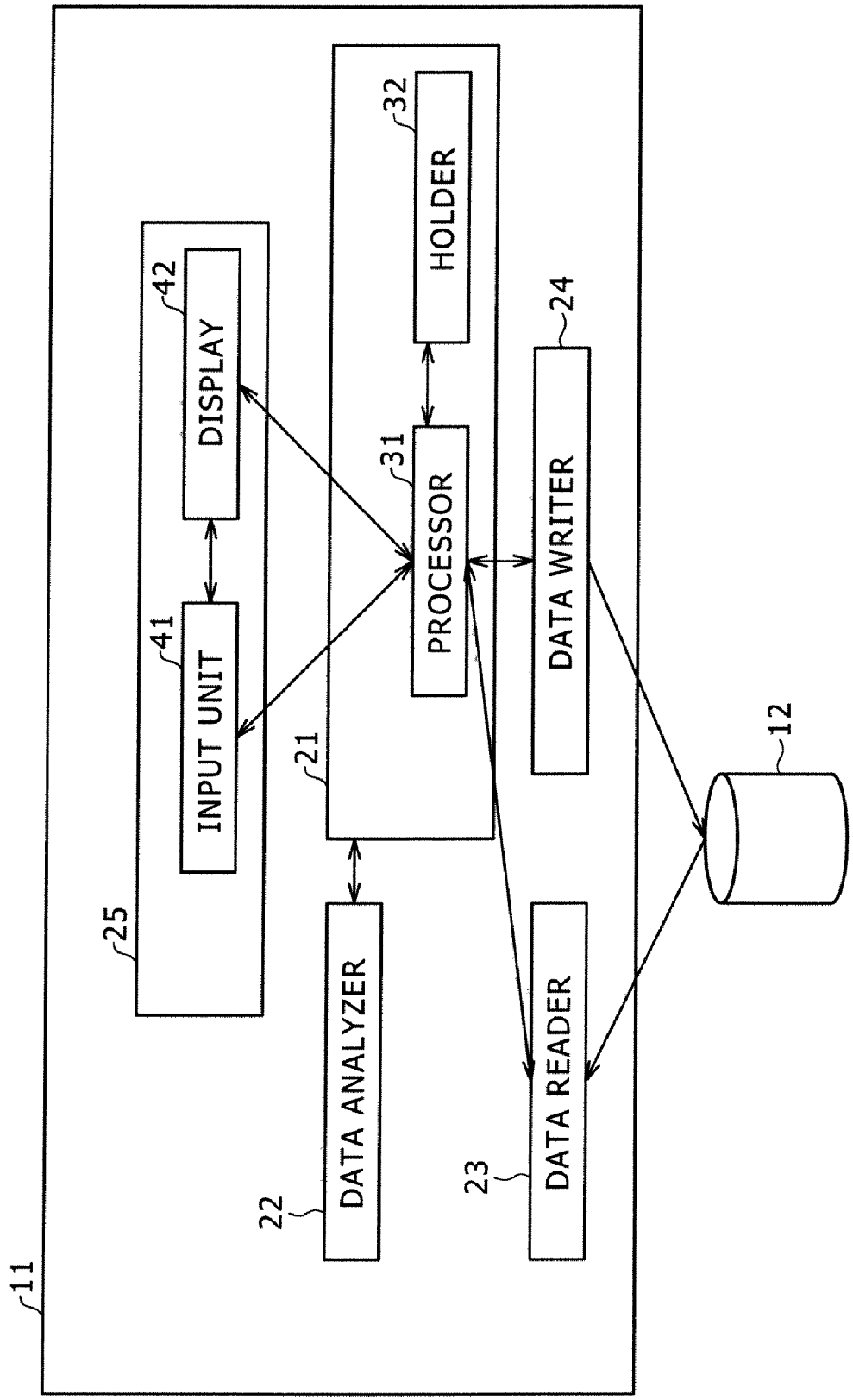
FIG. 1 is a block diagram of a functional arrangement of an information processing system including an information processing apparatus according to an embodiment of the present invention.

FIG. 1 shows in block form a functional arrangement of an information processing system including an information processing apparatus according to an embodiment of the present invention.

As shown in FIG. 1, the information processing system includes an information processing apparatus 11 and a database 12.

The information processing apparatus 11 detects one or more motifs from a protein network made up of a plurality of nodes and presents the detected motif or motifs to the user.

The nodes of the protein network represent proteins. As described later (see major intermediary nodes shown in FIG. 10), however, a node that exists at the same position in the same motif may not necessarily correspond to a protein of one type, but may correspond to proteins of a plurality of types. Except where the types of proteins are referred to, proteins will hereinafter be referred to simply as nodes.

Figure 2:
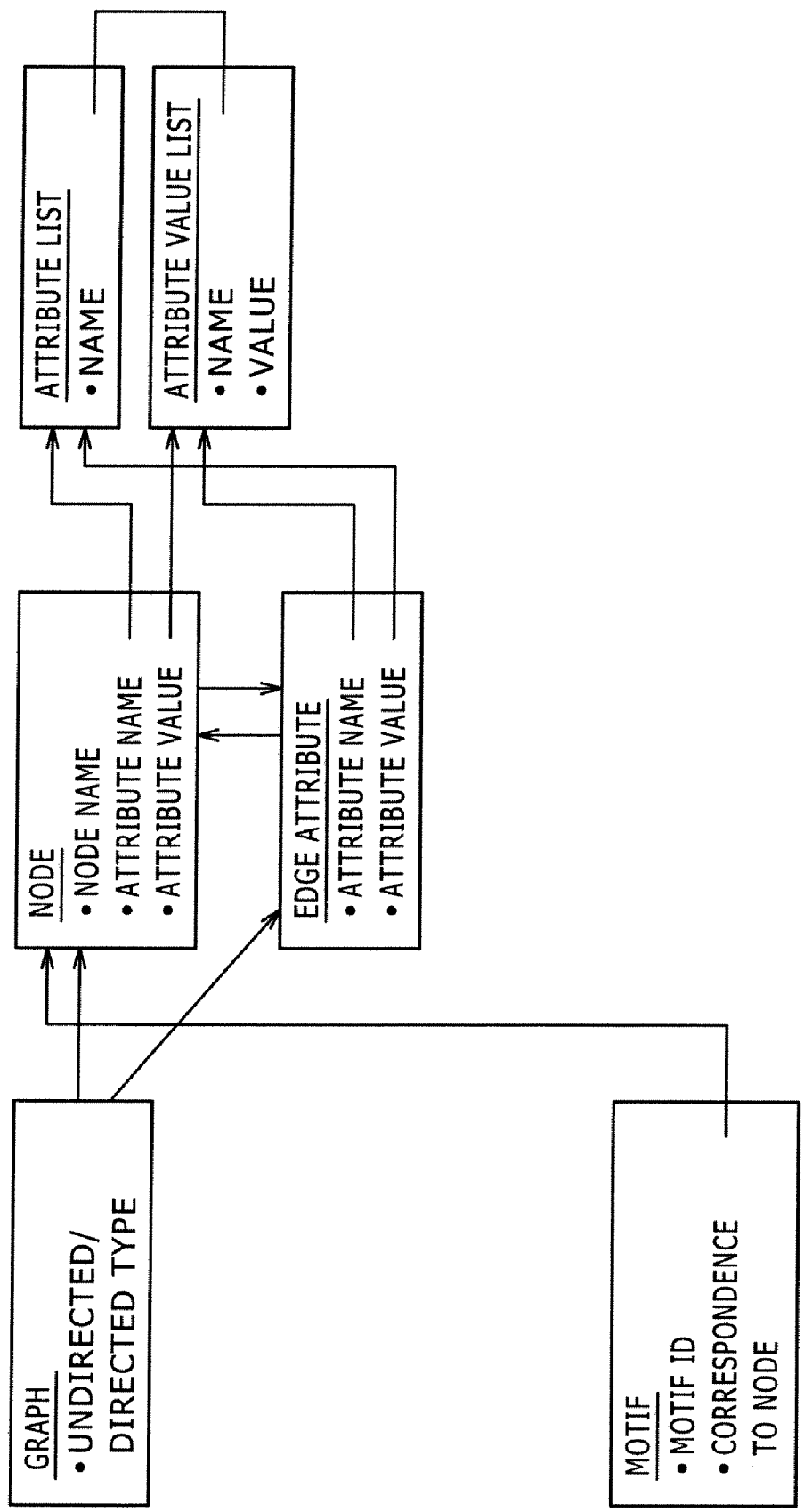
FIG. 2 is a block diagram showing by way of example a main data structure of data used by the information processing apparatus shown in FIG. 1.

The database 12 holds various data according to a data structure shown in FIG. 2. Specifically, FIG. 2 shows by way of example a main data structure of data used by the information processing apparatus 11 shown in FIG. 1. The phrase "main data structure of data used by the information processing apparatus 11" is employed because the data structure shown in FIG. 2 is used by the database 12, and also by a holder 32 in the information processing apparatus 11 as described later. All the data structure shown in FIG. 2 may not be constructed in the database 12, but may be constructed in the holder 32.

In FIG. 2, data contained in rectangular blocks including underscored character strings (graph, node, attribute list, etc.) are referred to as "character string data" based on their character strings. Specifically, the character string data are called "graph data", "node data", "attribute list data", "edge attribute data", "attribute value list data", and "motif data".

The "node data" are data for specifying a certain node, and include "node name", "attribute name", and "attribute value". A certain node can be specified based on "node name", "attribute name", and "attribute value" included in the "node data" thereof. The "node name" is data indicative of the name of the certain node, and may, for example, be data indicative of the name of a protein. The "attribute name" is data indicative of the name of an attribute of the certain node, e.g., data indicative of the name of an attribute to which the node is classified, among a plurality of attributes (e.g., a large molecule, a middle molecule, a small molecule, etc.) based on a certain feature of a protein. The "attribute value" is data indicative of a value corresponding to the "attribute name".

The "edge attribute data" are data indicative of an edge attribute assigned to a certain node.

The edge attribute refers to the following attribute. When a first node and a second node are to connect to each other, the first node may perform a certain action on the second node. An attribute classified depending on the type of the action is referred to as an edge attribute. Specifically, an edge attribute includes a first attribute and a second attribute.

The first attribute is an attribute for the first node to act to make the function of the second node positive (promote, strengthen, or increase the function of the second node). The name of the first attribute (attribute name) is represented by P.

The second attribute is an attribute for the first node to act to make the function of the second node negative (suppress, weaken, or reduce the function of the second node). The name of the second attribute (attribute name) is represented by N.

A unique value (attribute value) is given to P and N. According to the present embodiment, 2 is given as the attribute value of P, and 1 is given as the attribute value of N.

In summary, when the first node and the second node are to connect to each other, the first node performs an action on the second node. Data representing the type of the action (edge attribute) are referred to as "edge attribute data" with respect to the first node. The "edge attribute data" are made up of data of the "attribute name" and the "attribute value".

Similarly, when the second node acts on the first node, "edge attribute data" are produced with respect to the second node.

Since there are many types of proteins of a protein network, there are "node data" corresponding to the nodes (proteins) of the respective types. If a node of a certain type (a node specified by one "node data") can be connected to a plurality of other nodes (nodes specified by other "node data"), then since types (edge attributes) of actions on the respective other nodes are different from each other, there exist "edge attribute data" with respect to the respective other nodes.

Figure 8:
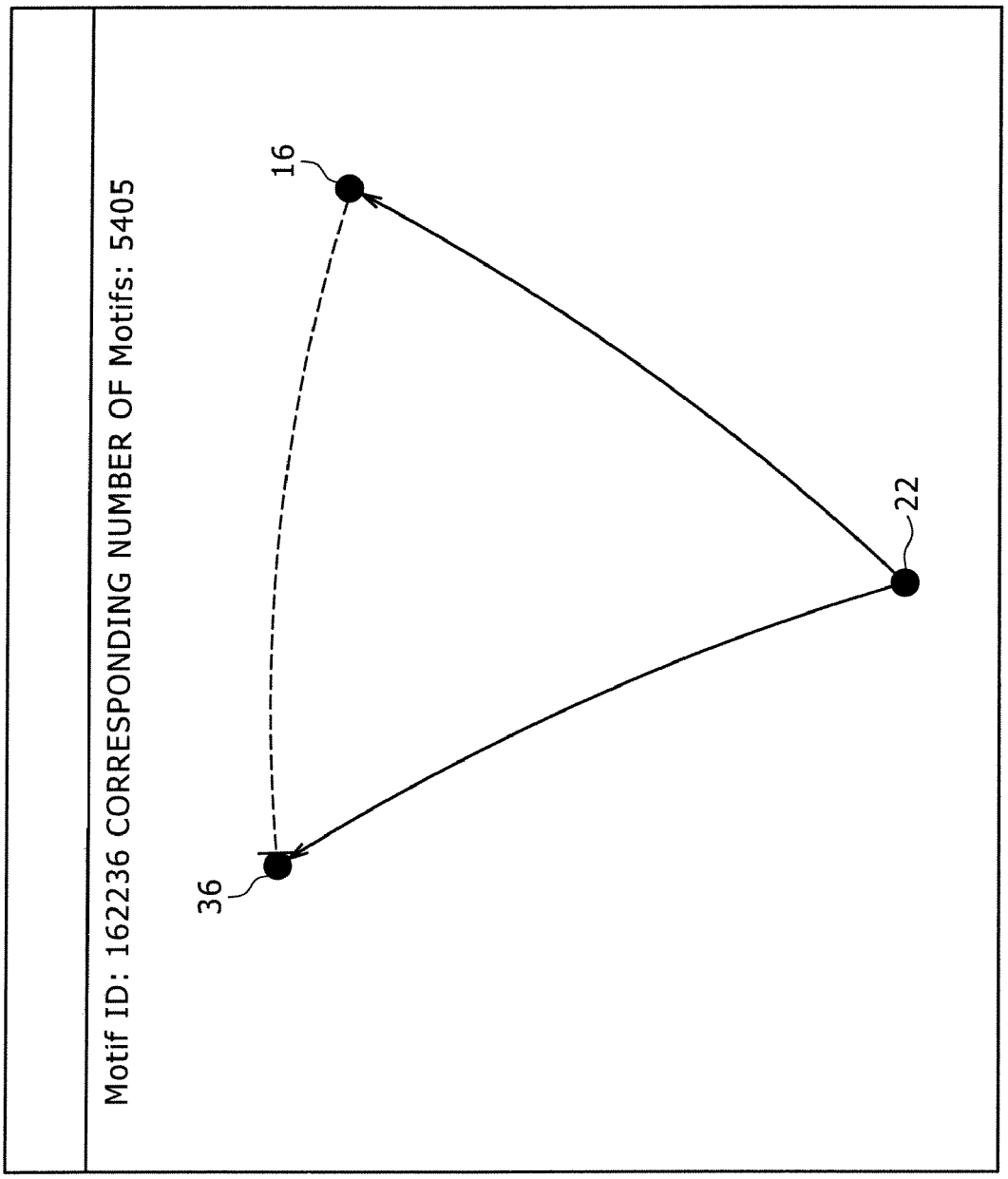
FIG. 8 is a diagram showing an example of the result of the motif displaying process shown in FIG. 7.

If an edge attribute of P or N is assigned to the first node, i.e., if the first node acts to make the second node positive or negative, then a link is provided from the first node to the second node. Data indicative of links from certain proteins to other proteins are stored as the "graph data" shown in FIG. 2. As shown in FIG. 8, when a link between two nodes is displayed, the link may be indicated by a directed arrow line or an undirected line. Such a directed or undirected line indicative of the link needs to be defined in advance. Data indicative of the defined directed or undirected line are stored as "undirected/directed type" as shown in FIG. 8.

Since a number of "node data" and "edge attributes" exist, there exist "attribute list data" representing a list of "attribute names" of "node data" and "attribute values" of "edge attributes", and "attribute value list data" representing a list of "attribute values" of "node data" and "attribute names" of "edge attribute data".

The "motif data" will be described later.

Various data are stored in the database 12 and the holder 32 shown in FIG. 1 according to the data structure shown in FIG. 2. Specific examples of various data will be described later with reference to FIG. 3 and other figures.

As shown in FIG. 1, the information processing apparatus 11 has the following first, second, and third functions.

The first function is a function to detect one or more motifs in a given protein network and generate information about the one or more motifs. The information about the one or more motifs is not limited to particular information, but represents the number of occurrences of each motif according to the present embodiment. The first function will hereinafter be referred to as a motif calculating function. A process that is realized by performing the first function is referred to as a motif calculating process. Details of the motif calculating process will be described later with reference to FIGS. 3 through 6.

The second function is a function to present the results of the motif calculating process to the user. According to the present embodiment, for example, the second function is a function to present, to the user, various detected motifs and the number of occurrences thereof on a display screen. The second function will hereinafter be referred to as a motif displaying function. A process that is realized by performing the motif displaying function is referred to as a motif displaying process. Details of the motif displaying function will be described later with reference to FIGS. 7 and 8.

The third function is a function to present, to the user, further detailed information about various motifs depending on the action made by the operator. According to the present embodiment, for example, the third function is a function to present, to the user, the detailed information about various motifs on a display screen. The third function will hereinafter be referred to as a motif details displaying function. A process that is realized by performing the motif details displaying function is referred to as a motif details displaying process. Details of the motif details displaying function will be described later with reference to FIGS. 9 through 13.

In order to perform the motif calculating function, the motif displaying function, and the motif details displaying function, the information processing apparatus 11 includes a data processor 21, a data analyzer 22, a data reader 23, a data writer 24, and a UI (User Interface) section 25.

These components of the information processing apparatus 11 will be described below. The data reader 23 reads various data from the database 12 and supplies the data to a processor 31 of the data processor 21 under the control of the data processor 21. The data writer 24 writes the various data provided from the processor 31 into the database 12 under the control of the data processor 21. Specific examples of the various data read from and written into the database 12 will be described later with reference to FIG. 3 and other figures.

The data analyzer 22 analyzes various data and supplies analytic results to the data processor 21 under the control of the data processor 21. Specific examples of the various data to be analyzed will be described later with reference to FIG. 3 and other figures.

The data processor 21 controls the data analyzer 22, the data reader 23, and the data writer 24 to process various data for the purpose of performing the motif calculating function, the motif displaying function, and the motif details displaying function. Specifically, various data are processed by the processor 31, and the data processed by the processor 31 and data to be used in various processes performed by the processor 31 are held in the holder 32. Specific examples of the various data to be processed will be described later with reference to FIG. 3 and other figures.

The UI section 25 provides a user interface to the user. Specifically, the UI section 25 functions as an interface between the user and the processor 31 of the data processor 21. Specifically, the UI section 25 includes an input unit 41 for the user to enter various pieces of information such as commands or the like, and a display 42 for presenting, to the user, various information on a display screen. Specific examples of the information entered through the input unit 41 and the information displayed on the display 42 will be described later with reference to FIG. 3 and other figures.

Details of the motif calculating function, the motif displaying function, and the motif details displaying function will be described below in the order named.

Of the processes for performing the motif calculating function, the motif displaying function, and the motif details displaying function, the process for the processor 31 to control the data analyzer 22, etc. may be carried out by the processor 31 itself. Conversely, the processes carried out by the processor 31 itself may be performed by controlling the data analyzer 22, etc. with the processor 31.

First, details of the motif calculating function will be described below with reference to FIGS. 3 through 6.

Figure 3:
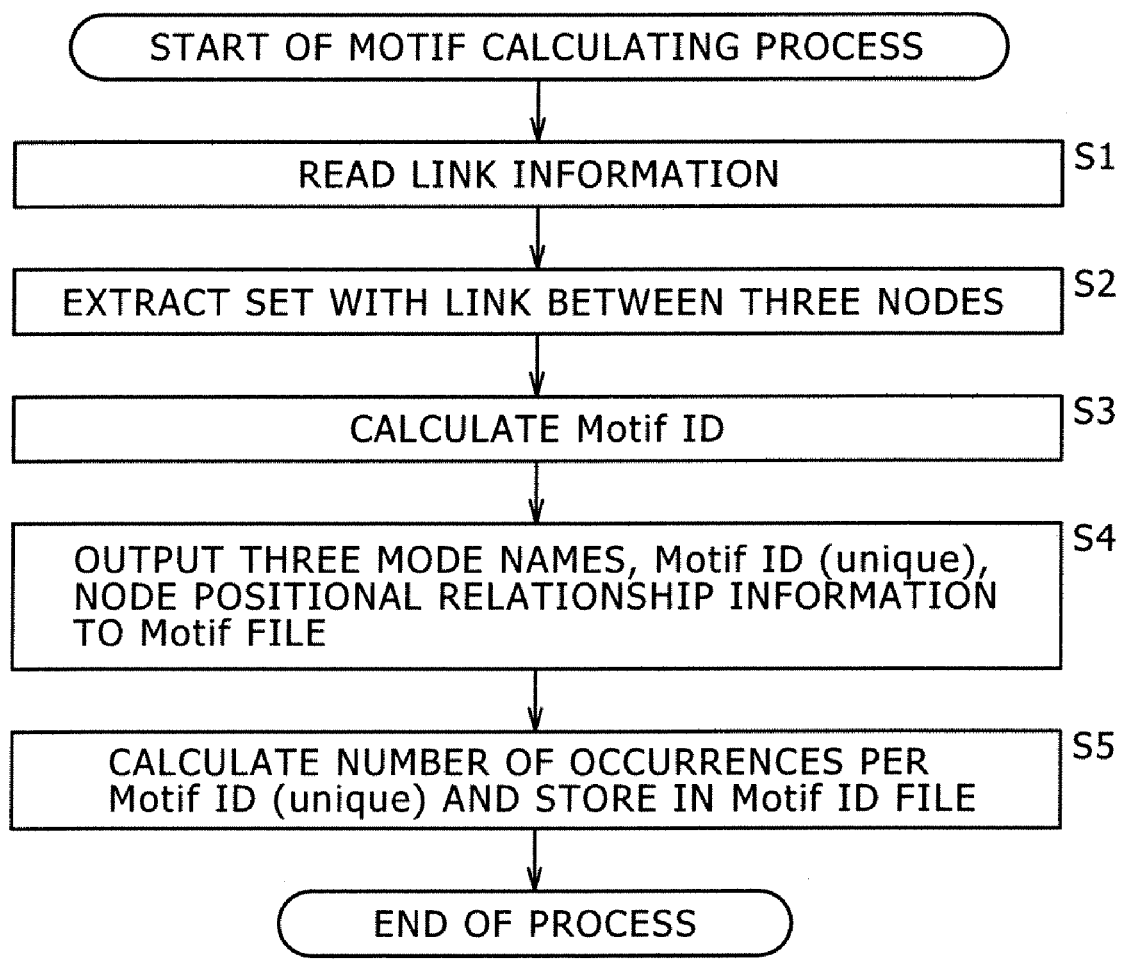
FIG. 3 is a flowchart of a motif calculating process among the processes performed by the information processing apparatus shown in FIG. 1.

FIG. 3 is a flowchart of the motif calculating process.

In step S1, the processor 31 controls the data reader 23 to read link information from the database 12 and holds the link information in the holder 32.

The link information is information representing contents of a link between a first node and a second node. Specifically, the link information includes the "first node", an "edge attribute about the second node with respect to the first node", and the "second node".

For the "first node", the "node name" of the "node data" with respect to the first node in terms of the example shown in FIG. 2 may be employed.

For the "edge attribute about the second node with respect to the first node", the "attribute name" or the "attribute value" of the "edge attribute data" about the second node with respect to the first node is employed. According to the present embodiment, for example, the "attribute value" is employed in order to facilitate the calculation of a Motif ID to be described later.

For the "second node", the "node name" of the "node data" with respect to the second node in terms of the example shown in FIG. 2 may be employed.

The processor 31 can read one of a plurality of "node data" stored in the database 12, as the "node data" of the first node, with the "node name" representing the "first node".

The second node linked from the first node can be specified from the "graph data" shown in FIG. 2. Based on the "graph data", the processor 31 can specify the second node and read the "node name" of the "node data" with respect to the second node as the "second node". The processor 31 can read the "attribute value" of the "edge attribute data" about the second node with respect to the first node, as the "edge attribute about the second node with respect to the first node".

In this manner, one link information is read.

As described above, the second node linked from the first node is not limited to a node of one type, but may often include nodes of many types. Therefore, the number of pieces of link information with respect to the first node is equal to the number of types linked from the first node.

Since each of proteins of plural types can be the first node, i.e., each of the "node data" stored in the database 12 can be the first node, the link information about each of nodes of different types that are linked is read per each of the "node data".

For reading each link information, the "attribute list data" and the "attribute value list data" may be employed rather than the "node data" and the "edge attribute data" themselves.

Each link information may be produced in advance and may be held in the database 12.

When each link information is held in the holder 32, control goes from step S1 to step S2.

In step S2, the processor 31 extracts a set with links between three nodes, based on each link information.

The set with link between three nodes is a set forming a triangle with the three nodes at the respective vertexes, with a link provided from at least one of two vertexes (two nodes) to the other on each of the three sides of the triangle, i.e., with at least one of two vertexes acting to make the function of the other node positive/negative.

In other words, each set extracted in step S2 represents motifs between three nodes in a protein network.

In step S3, processor 31 calculates an ID with respect to each motif (hereinafter referred to as "Motif ID").

A specific example of the calculation of a Motif ID will be described below. A process of calculating a Motif ID in step S3 is divided into the following steps S3a through S3d.

In step S3a, the processor 31 converts edge attributes assigned respectively to "in", "out" into numerical values with respect to each of the three nodes making up motifs, per each of the two other nodes connected thereto. "in", "out" will be described later. Specifically, the processor 31 expresses an edge attribute according to the ternary notation with respect to a given node, i.e., expresses an edge attribute as "1" if the node has an edge attribute of N, expresses an edge attribute as "2" if the node has an edge attribute of P, and expresses an edge attribute as "0" if the node has no edge attribute, in relation to another node connected to the node, per each of "in", "out". The processor 31 then produces numerical values calculated by (in_num*3+out_num) where in_num, out_num are ternary representations of "in", "out". These numerical values will hereinafter be referred to as link numerical values.

Here, "in", "out" are defined as follows. Of three nodes making up motifs, two nodes are referred to as a first node and a second node, and a connection therebetween is taken into consideration. A link may be provided from the first node to the second node, and a link may also be provided from the second node to the first node. In other words, the first node may act to make the function of the second node positive/negative, and the second node may act to make the function of the first node positive/negative. From the standpoint of the first node in relation to the second node connected thereto, the first node may act on the second node connected thereto and may be acted on from the second node. The former action is referred to as "out", and the action received as "in".

Between the first node and the second node, links may not necessarily be provided in both directions, but a link may be provided in one direction.

From the standpoint of the first node in relation to the second node connected thereto, the first node is grasped as being assigned an edge attribute of P or N or no edge attribute with respect to "in", or as being assigned an edge attribute of P or N or no edge attribute with respect to "out".

Designations with respect to a node thus grasped include a succession of character strings of "edge attribute (P or N) assigned to "in"", "in", "edge attribute (P or N) assigned to "out"", and "out".

Specifically, for example, the first node is described as "P in N out". "P in N out" means, as seen from the first node, receiving an action to make the function of the first node positive from the second node (the function of the first node is made positive) and providing an action to make the function of the second node negative.

If the first node is described as "P in", then it means, as seen from the first node, receiving an action to make the function of the first node positive from the second node (the function of the first node is made positive) and providing no action to the second node (the function of the second node is made neither positive nor negative). If "N out" is employed, then it means, as seen from the first node, receiving no action from the second node (the function of the first node is made neither positive nor negative) and providing an action to make the function of the second node negative.

When the first node and the second node are connected to each other, if the first node is described as "P in N out", then the second node as "N in P out". If the first node is described as "P in", then the second node as "P out", and if the first node is described as "N out", then the second node as "N in".

Numerical values representing "P in N out", "P in", "N out", etc. are referred to as link numerical values.

Specifically, a link numerical value of "P in N out" is 2*3+1=7 because in_num=2 (=P) and out_num=1 (=N). A link numerical value of "P in" is 2*3+0=6 because out_num=0, and a link numerical value of "N out" is 0*3+1=1 because in_num=0.

The holder 32 may hold a table shown in FIG. 4, and a process of reading a corresponding value from the link numerical values in the table shown in FIG. 4 may be performed in step S3a.

It is assumed that a triangle wherein three nodes making up motifs are disposed at the respective vertexes is formed, the position of one of the vertexes (e.g., an upper right black dot marked with a numerical value of 16 in FIG. 8) is represented by v1, and the positions of the other two vertexes (e.g., an upper left black dot marked with a numerical value of 36 and a lower central black dot marked with a numerical value of 22 in FIG. 8) arranged successively counterclockwise from the vertex at the position v1 are represented by v2, v3, respectively.

The position v1 will be taken into consideration. The node at the position v1 has two link numerical values, i.e., a link numerical value with respect to the node at the position v2 and a link numerical value with respect to the node at the position v3.

In step S3b, the processor 31 produces a two-figure numerical value (hereinafter referred to as "node link numerical value) with a tens-place digit represented by a larger one of the link numerical value of the node at the position v1 with respect to the node at the position v2 and the link numerical value of the node at the position v1 with respect to the node at the position v3, and a ones-place digit represented by a smaller one of these link numerical values.

Specifically, for example, if the node at the position v1 is described as "P in N out" with respect to the node at the position v2 and as "N out" with respect to the node at the position v3, then the link numerical value of the node at the position v1 with respect to the node at the position v2 is 7, and the link numerical value of the node at the position v1 with respect to the node at the position v3 is 1. In this case, a two-figure numerical value of 17 is produced as the node link numerical value of the node at the position v1 in step S3b.

Similarly, in step S3b, the processor 31 produces respective node link numerical values of the nodes at the positions v2, v3.

In step S3c, the processor 31 produces a numerical sequence of the node link numerical values of the nodes at the positions v1, v2, v3 in a predetermined order, e.g., in the order named in the present embodiment, the numerical sequence being represented by MotifID(original). Specifically, if the node link numerical values of the nodes at the positions v1, v2, v3 are represented by v1_node_num, v2_node_num, v3_node_num, respectively, then the numerical sequence (v1_node_num v2_node_num v3_node_num) is represented by MotifID(original).

Specifically, if the node link numerical values v1_node_num, v2_node_num, v3_node_num are 48, 47, 58, respectively, then the numerical sequence MotifID(original) is "484758".

In step S3d, the processor 31 produces a numerical sequence made up of the node link numerical values of the nodes at the positions v1, v2, v3 where the node link numerical values are arranged in ascending order, the numerical sequence being represented by MotifID(unique).

Specifically, in the above example, since the node link numerical values v1_node_num, v2_node_num, v3_node_num are 48, 47, 58, respectively, the numerical sequence MotifID(unique) is "474858".

The numerical sequence MotifID(original) is an ID capable of identifying the positional relationship of the three nodes, whereas the numerical sequence MotifID(unique) is an ID not related to the positional relationship of the three nodes. It is convenient if information capable of grasping the positional relationship of the three nodes, i.e., information representative of an association between MotifID(original) and MotifID(unique) (hereinafter referred to as "node positional relationship information"), is produced from the numerical sequence MotifID(unique). According to the present embodiment, therefore, the processor 31 also generates node positional relationship information with respect to the generated numerical sequence MotifID(unique) in step S3d.

The node positional relationship information is not limited to any format. According to the present embodiment, however, information indicating which of the node link numerical values v1_node_num, v2_node_num, v3_node_num each of the numerical values of upper two figures, middle two figures, and lower two figures of the six-figure numerical sequence of the numerical sequence MotifID(unique) corresponds to, is employed as the node positional relationship information.

Specifically, of the six-figure numerical sequence of the numerical sequence MotifID(unique), the upper two figures, middle two figures, and lower two figures are indicated by 1, 2, 3, respectively, and information indicating the relationship between (1, 2, 3) and (v1_node_num, v2_node_num, v3_node_num) is employed as the node positional relationship information.

More specifically, in the above example, node link numerical values v1_node_num, v2_node_num, v3_node_num are 48, 47, 58, respectively, and hence the numerical sequence MotifID(unique) is "474858". In this case, the upper two figures (=1) are represented by v1_node_num (=47), the middle two figures (=2) by v2_node_num (=48), and the lower two figures (=3) by v3_node_num (58). Information indicative of (v1_node_num, v2_node_num, v3_node_num)= (2, 1, 3) is generated as the node positional relationship information.

If a MotifID is simply described, then it means that there is no distinction between MotifID(unique) and MotifID(original), or it includes both MotifID(unique) and MotifID(original).

After a MotifID is calculated in steps S3a through S3d, i.e., in step S3 shown in FIG. 3, then control goes to step S4.

In step S4, the processor 31 outputs the three node names, the numerical sequence MotifID(unique), and the node positional relationship information per motif to a given file (hereinafter referred to as "Motif file").

The storage location for the Motif file may be the database 12 or the holder 32. If the storage location for the Motif file is the database 12, then the processor 31 controls the data writer 24 to store the three node names, the numerical sequence MotifID(unique), and the node positional relationship information as a Motif file in the database 12.

For example, a Motif file shown in FIG. 5 is stored in the database 12 or the holder 32.

In the Motif file shown in FIG. 5, each row corresponds to a motif.

The column "THREE NODE NAMES" contains subcolumns "v1", "v2", "v3". The subcolumn "v1" stores the names of the nodes existing at the position v1, the subcolumn "v2" the names of the nodes existing at the position v2, and the subcolumn "v3" the names of the nodes existing at the position v3. Specifically, of the link information read in step S1, the "node names" of the "node data" shown in FIG. 2 with respect to the nodes that exist at the positions v1, v2, v3 are stored in the subcolumns "v1", "v2", "v3".

In the Motif file shown in FIG. 5, the column "MotifID (original)" is provided for an easier understanding of the invention. However, since the numerical sequence MotifID (original) can be reproduced from the numerical sequence MotifID(unique) and the node positional relationship information, the column "MotifID(original)" is not indispensable in the Motif file.

The columns "MotifID(unique)" and "NODE POSITIONAL RELATIONSHIP INFORMATION" store numerical sequences MotifID(unique) and node positional relationship information generated in step S3d. For example, it can be seen from FIG. 5 that the numerical sequences MotifID(unique) and the node positional relationship information given in the above specific example are stored in these columns for the motif in the second row.

In step S5 shown in FIG. 3, the processor 31 controls the data analyzer 22 to calculate the number of occurrences per MotifID(unique), and stores calculated results in a given file (hereinafter referred to as "MotifID file").

The storage location for the MotifID file may be the database 12 or the holder 32. If the storage location for the MotifID file is the database 12, then the processor 31 controls the data writer 24 to store the number of occurrences per MotifID (unique) as a MotifID file in the database 12.

For example, a MotifID file shown in FIG. 6 is stored in the database 12 or the holder 32.

The motif calculating process is now finished.

The information stored in the Motif file and the MotifID file thus generated corresponds to "motif data" referred to in FIG. 2.

The details of the motif calculating function have been described above with reference to FIGS. 3 through 6.

Details of the motif displaying function will be described below with reference to FIGS. 7 and 8.

Figure 7:
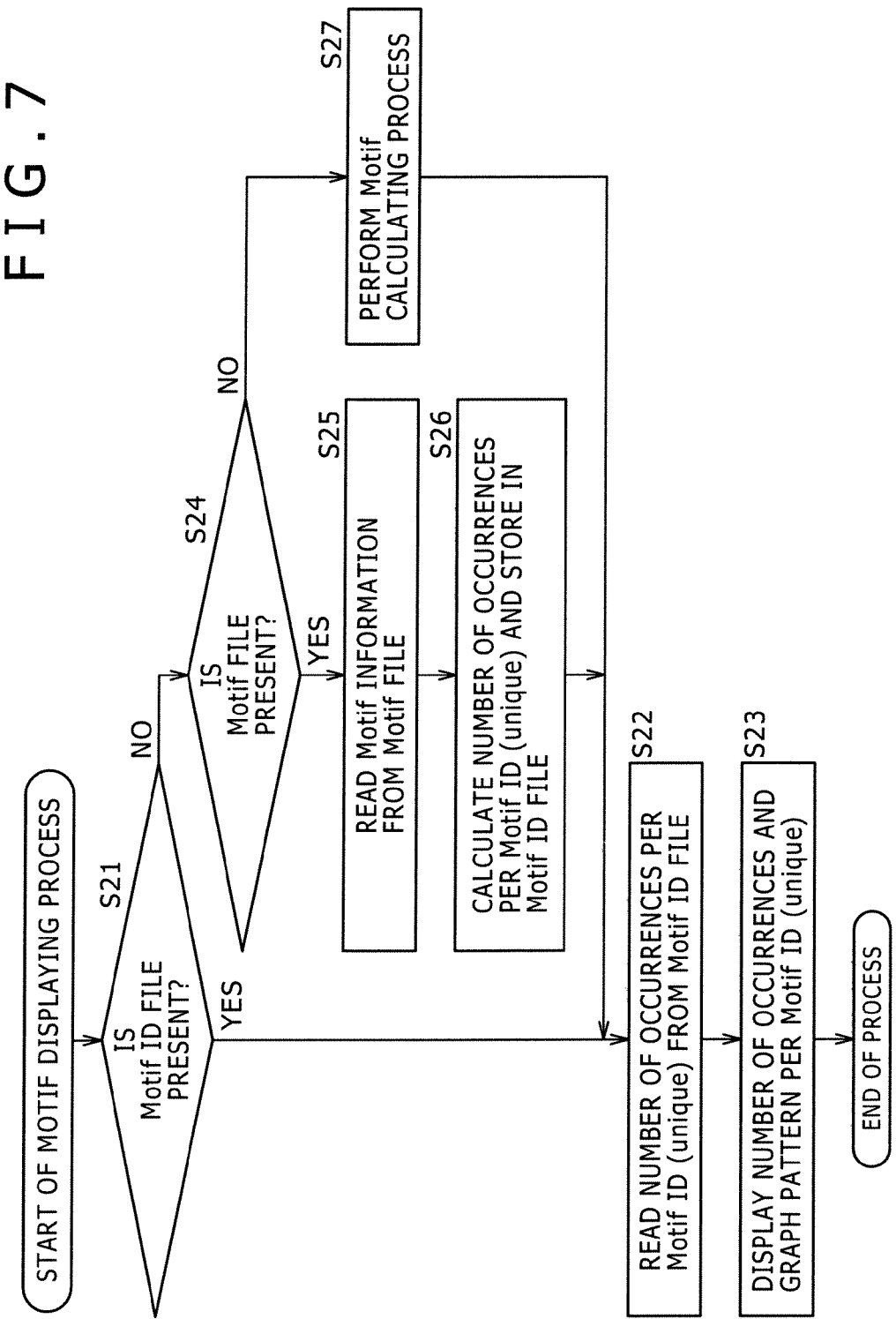
FIG. 7 is a flowchart of a motif displaying process among the processes performed by the information processing apparatus shown in FIG. 1.

FIG. 7 is a flowchart of the motif displaying process.

In step S21 shown in FIG. 7, the processor 31 shown in FIG. 1 determines whether a MotifID file (see FIG. 6) is present or not.

If a MotifID file is present, then the answer to step S21 is YES, and control goes to step S22.

In step S22, the processor 31 reads the number of occurrences per MotifID(unique) from the MotifID file. If the MotifID file is stored in the database 12, then the processor 31 controls the data reader 23 to read the number of occurrences per MotifID(unique) from the MotifID file in the database 12.

In step S23, the processor 31 controls the display 42 to display the number of occurrences and a graph pattern per MotifID(unique).

The number of occurrences and the graph pattern are not limited to any display format. According to the present embodiment, however, the display format shown in FIG. 8 is employed. Specifically, FIG. 8 shows a displayed example of the number of occurrences and the graph pattern for a motif whose MotifID(unique) is "162236" among the motifs between the three nodes of a protein network.

In the example shown in FIG. 8, a message displayed to the right of the message "MotifID: 162236", i.e., "CORRESPONDING NUMBER OF Motifs: 5405", displays the number of occurrences. It can be seen from the displayed message that the number of occurrences of the motif whose MotifID (unique) is "162236" is "5405".

In the example shown in FIG. 8, the graph pattern of the motif whose MotifID(unique) is "16223" is displayed below the displayed number of occurrences of the motif.

The graph pattern includes three nodes indicated by black dots and links between two nodes indicated by a solid line or a dotted line.

If it is assumed that an arrowheaded one of the two ends of a solid line is referred to as a distal end and the other end (not arrowheaded) as a proximal end, then the solid line represents a link (hereinafter referred to as "P link") which is provided when a first node at the proximal end acts to make the function of a second node at the distal end positive. If it is assumed that one with a vertical line of the two ends of a dotted line is referred to as a distal end and the other end (not with a vertical line) as a proximal end, then the dotted line represents a link (hereinafter referred to as "B link") which is provided when a first node at the proximal end acts to make the function of a second node at the distal end negative.

Of the three nodes (black dots), the upper right node represents the node at the position v1, the upper left node represents the node at the position v2, and the lower middle node represents the node at the position v3. The node link numerical values produced in step S3b are displayed respectively near the three nodes.

With the graph pattern being thus displayed, the details of the links at the nodes making up the motif can easily be recognized, i.e., the relationship between the positive and negative functions between the three nodes (proteins) can easily be recognized.

In FIG. 7, if the answer to step S21 is NO, i.e., if no MotifID file is present, in step S21, then control goes to step S24.

In step S24, the processor 31 determines whether a Motif file (see FIG. 5) is present or not.

If a MotifID file is not present, but a Motif file is present, then the answer to step S24 is YES, and control goes to step S25.

In step S25, the processor 31 reads Motif information from the Motif file. If the Motif file is stored in the database 12, then the processor 31 controls the data reader 23 to read Motif information from the Motif file in the database 12. The Motif information represents the three node names, the numerical sequence MotifID(unique), and the node positional relationship information per motif. In the example shown in FIG. 5, the information of a corresponding row is read as Motif information per motif.

In step S26, the processor 31 controls the data analyzer 22 to calculate the number of occurrences per MotifID(unique), and stores calculated results in a MotifID file. Therefore, step S26 corresponds to step S5 of the motif calculating process shown in FIG. 3.

After the processing in step S is performed, i.e., when the MotifID file and the Motif file exist, control goes to step S22, and the processing from step S22 is performed.

If neither MotifID file nor Motif file exists, then the answer to step S24 is NO, and control goes to step S27.

In step S27, the processor 31 carries out the motif calculating process in step S3. When the motif calculating process is performed, i.e., when the MotifID file and the Motif file exist, control goes to step S22, and the processing from step S22 is performed.

The details of the motif displaying function has been described above with reference to FIGS. 7 and 8.

Details of the motif details displaying function will be described below with reference to FIGS. 9 through 13.

Figure 9:
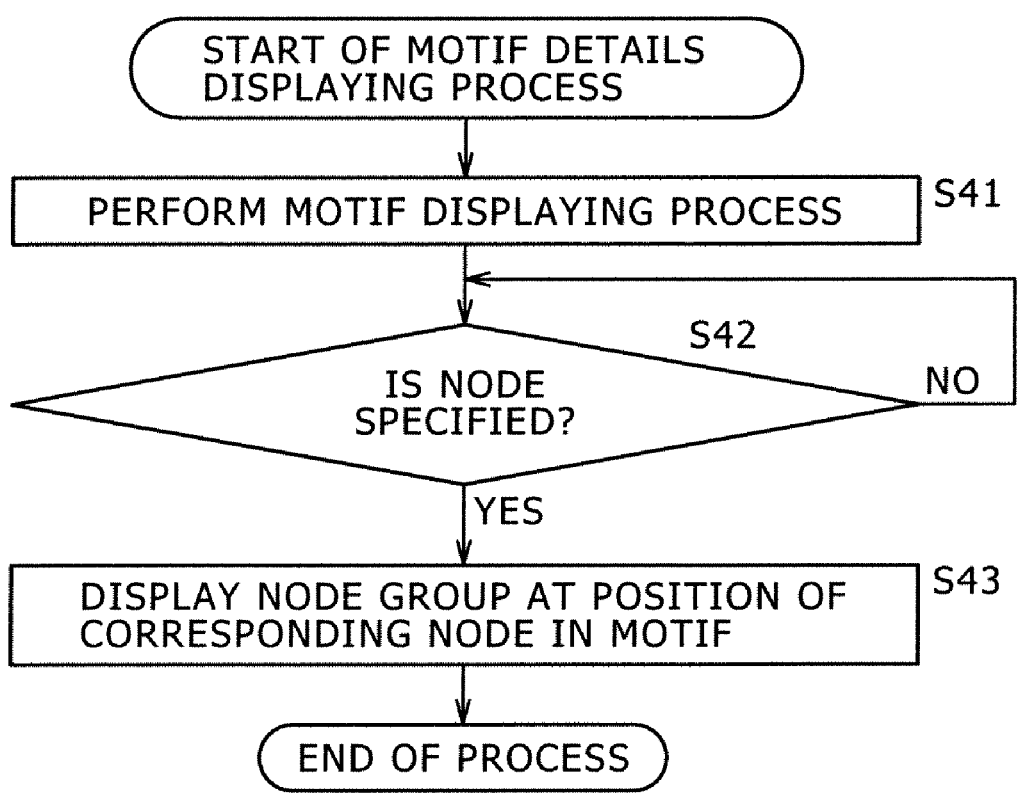
FIG. 9 is a flowchart of a motif details displaying process among the processes performed by the information processing apparatus shown in FIG. 1.

FIG. 9 is a flowchart of the motif details displaying process.

In step S41 shown in FIG. 9, the processor 31 shown in FIG. 1 performs the motif displaying process shown in FIG. 7.

According to the motif displaying process, the number of occurrences and a graph pattern per MotifID(unique) are displayed on the display 42 in the display format shown in FIG. 8, for example, in the present embodiment.

As described above, according to the graph pattern of a motif having a given MotifID(unique), black dots are displayed as indicating the three modes making up the motif.

At this stage, each node is represented by a simple black dot and is silent as to which type of protein it is made up of.

According to the motif details displaying process shown in FIG. 9, steps S42, S43 are carried out to display a collection of proteins that can make up a node specified by the user. The collection of proteins that can make up a given node will hereinafter referred to as "node group". Displaying a node group means displaying information capable of identifying proteins that can make up a certain node, e.g., the names or the like of those proteins.

In step S42, the processor 31 determines whether the user has specified a node or not.

The user may specify a node according to any processes. According to a node specifying process used in the present embodiment, at least a portion of the input unit 41 includes a mouse, and the user uses the mouse to click on one of the three nodes (black dots) included in the graph pattern displayed on the display 42, as a node to be specified, thereby specifying the node.

Until a desired not is clicked on, the answer to step S42 is NO, and control goes back to step S42 to determine again whether the user has specified a node or not.

If a desired not is clicked on, the answer to step S42 is YES, and control goes to step S43.

In step S43, the processor 31 displays a node group at the position of the node in the motif on the display 42. Specifically, the names or the like of proteins that can be the node specified in step S42 are displayed on the display 42.

Specifically, it is assumed that when the motif calculating process shown in FIG. 3 is carried out, eight numerical sequences MotifID(unique) shown in FIG. 10 are calculated, for example, and graph patterns and the numbers of occurrences shown in FIG. 10 with respect to the eight numerical sequences MotifID(unique) are displayed in one window (see FIG. 8) on the display 42 according to the motif displaying process in step S41.

Though the three nodes (black dots) are omitted from illustration in FIG. 10, they are actually displayed on the display 42. In the example shown in FIG. 10, the uppermost (upper right) node is at the position v1, the central (central left) node is at the position v2, and the lowermost (upper right) node is at the position v3. However, insofar as the positions v1, v2, v3 are arranged successively counterclockwise, the position v1 is not limited to the illustrated position. Furthermore, if the definition of a Motif file is changed, then it is not necessary to employ the counterclockwise arrangement of the positions v1, v2, v3. In the example shown in FIG. 10, the numbers of occurrences are displayed as percentages. However, the numbers of occurrences may be displayed as absolute numbers as shown in FIG. 8.

It is assumed that the user pays attention to a motif whose number of occurrences is the greatest (whose percentage is the greatest), i.e., a motif whose MotifID(unique) is "222666", and clicks on the node at the position v2 (not shown in FIG. 10, see the black dot in FIG. 8) in order to recognize a node group at the position v2 (the position indicated by a circle in FIG. 10).

In step S42, the answer is judged as YES, and the information in the column "MAJOR INTERMEDIARY NODES" shown in FIG. 10, i.e., "JUN SP1, TP53 SP3 Transcription Factor", is displayed on the display 42 as a node group at the position of the corresponding node (the position indicated by the circle in FIG. 10) in the motif whose MotifID(unique) is "222666" in step S43.

Therefore, the user can quickly recognize, through a simple action, that "JUN SP1, TP53 SP3 Transcription Factor" are present as proteins (nodes) working as an intermediary among important structures whose frequency of occurrences is high in a protein network.

Specifically, heretofore, there has been a theory showing that nodes (proteins) working as an intermediary among important structures whose frequency of occurrences is high are nodes playing an important role. However, a large expenditure of time and labor has been demanded to find actual proteins that match the theory from a given protein network.

Specifically, even if an analysis is performed by the technology disclosed in the non-patent document 1 described above, since the concept of "positive/negative" is not introduced for a link between two nodes, the motif having the upper left graph pattern shown in FIG. 10 may not be detected. It is then assumed that the concept of "positive/negative" is introduced into the technology disclosed in the non-patent document 1. According to the assumption, it still demands a large expenditure of time and labor to detect each of the eight motifs shown in FIG. 10 and to find that the motif having the leftmost graph pattern in FIG. 10, i.e., the motif with the MotifID(unique) of "222666" assigned thereto according to an embodiment of the present invention, is an important structure whose frequency of occurrences is high. Consequently, a huge expenditure of time and labor is requisite to specify a node group working as an intermediary, i.e., a node group at the position v2 (the position indicated by the circle in FIG. 10), in the motif.

According to an embodiment of the present invention, however, the information processing apparatus 11 (FIG. 1) is used to perform the motif calculating process (FIG. 3), the motif displaying process (FIG. 7), and the motif details displaying process (FIG. 9) for the user to recognize that "JUN SP1, TP53 SP3 Transcription Factor" are present as proteins (nodes) working as an intermediary among important structures whose frequency of occurrences is high, in a short time through an easy process.

In the example shown in FIG. 10, a position to display a node group is specified by clicking the mouse. However, such a position may be specified by any processes insofar as they are basically capable of specifying MotifID(unique) and the position of a node in a motif (e.g., any one of the positions v1, v2, v3 in the present embodiment).

Figure 11:
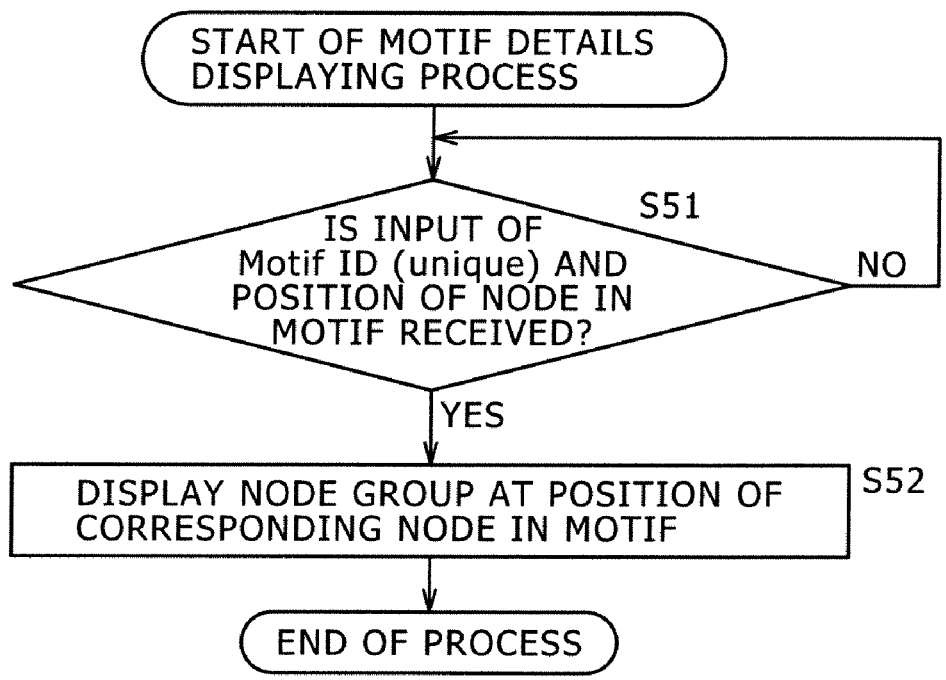
FIG. 11 is a flowchart of another motif details displaying process, which is different from the motif details displaying process shown in FIG. 9, among the processes performed by the information processing apparatus shown in FIG. 1.

For example, the user may directly enter MotifID(unique) and the position of a node in a motif using the input unit 41 (FIG. 1) which includes a keyboard or the like, thereby specifying a position to display a node group. FIG. 11 is a flowchart of a motif details displaying process, different from the motif details displaying process shown in FIG. 9, to be performed when a position to display a node group is specified as described above.

In step S51 shown in FIG. 11, the processor 31 shown in FIG. 1 determines whether the input of MotifID(unique) and the position of a node in a motif is received or not.

Until the input is received, the processor 31 repeatedly performs a loop process for judging the answer to step S51 as NO and returning control to step S51.

If the input is received, the processor 31 judges the answer to step S51 as YES, and controls the display 42 to display a node group at the position of the node in the motif in step S52.

It is convenient for the user if a protein network can be analyzed to find what are most frequent roles/positions among the roles/positions of a motif as a feature of a certain protein (node). For allowing the user to make such an analysis quickly and simply, the information processing apparatus 11 shown in FIG. 1 may perform a motif details displaying process shown in FIG. 12, which is different from the motif details displaying processes shown in FIGS. 9 and 11.

Figure 12:
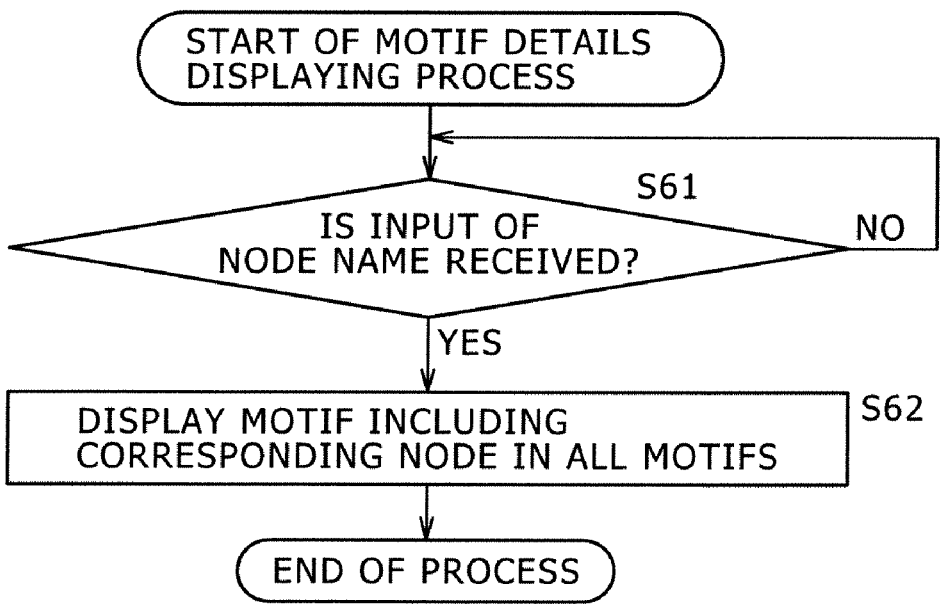
FIG. 12 is a flowchart of still another motif details displaying process, which is different from the motif details displaying processes shown in FIGS. 9 and 11, among the processes performed by the information processing apparatus shown in FIG. 1.

In step S61 shown in FIG. 12, the processor 31 shown in FIG. 1 determines whether the input of a node name is received or not.

The node name refers to the name of a certain protein (node) to be analyzed by the user, i.e., "SP2", "TP53", or the like. Specifically, the user can directly enter the name of a certain protein (node) to be analyzed, using the input unit 41 (FIG. 1) which includes a keyboard or the like.

Until the input is received, the processor 31 repeatedly performs a loop process for judging the answer to step S61 as NO and returning control to step S61.

If the input is received, the processor 31 judges the answer to step S61 as YES, and controls the display 42 to display a motif including the node (the node specified by the node name received in step S61) among all the motifs in step S62.

Specifically, in step S62, the processor 31 controls the data analyzer 22 to retrieve one or more MotifID(unique) corresponding to one or more motifs including the node from the Motif file or the like, and controls the display 42 to display each motif specified by the one or more MotifID(unique).

Figure 13:
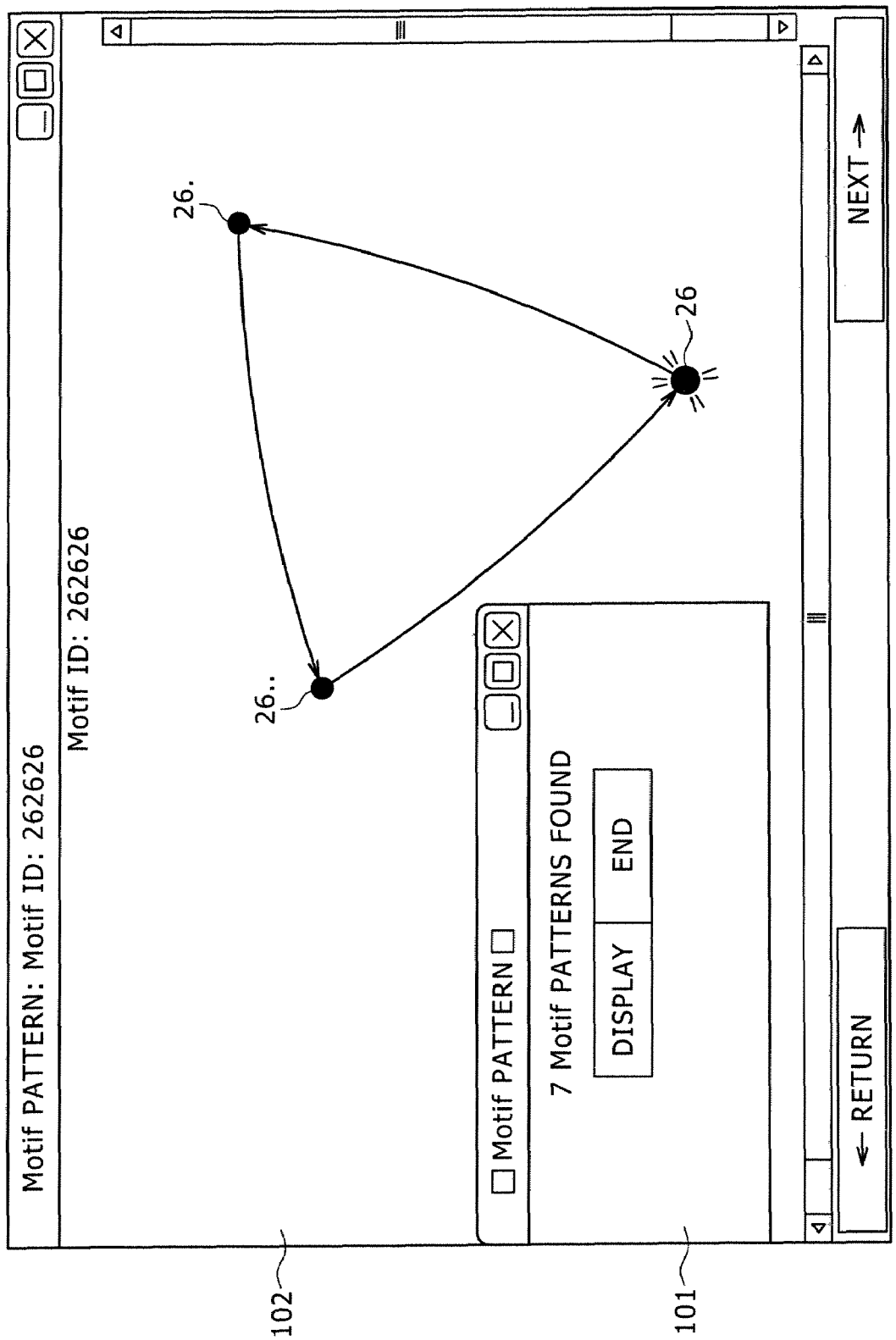
FIG. 13 is a diagram showing an example of the result of the motif details displaying process shown in FIG. 12.

The displayed motifs are not limited to any display format. According to the present embodiment, however, the display format shown in FIG. 13 is employed. Specifically, FIG. 13 shows a displayed example of motifs including a certain node (protein) specified by the user, of the motifs between three nodes of a protein network.

In the example shown in FIG. 13, the display 42 displays a window showing the total number of motifs including certain nodes (proteins) specified by the user, and a window 102 showing MotifID (unique) and a graph pattern about one of the motifs.

The user can easily visually recognize that there are seven motifs including the certain node (protein) specified by the user, by viewing the window 101. When the user presses a software button "DISPLAY" in the window 101, MotifID (unique) and a graph pattern of one of the seven motifs are displayed in the window 102. When the user presses the software button "DISPLAY" in the window 101 again, MotifID(unique) and a graph pattern of another one of the seven motifs are displayed in the window 102. If the user wants to end the display, the user may press a software button "END" in the window 101.

The lower central node (the node at the position v3) among the three nodes (black dot) in the window 102 shown in FIG. 13 is represented by a larger black dot than the other nodes, and is displayed in a flickering manner to distinguish the certain node specified by the user from the other nodes. The display format of the certain node specified by the user is not limited to the illustrated display format shown in FIG. 13 and may be of any display format insofar as it distinguishable from the display format of the other nodes. For example, the certain node specified by the user may be displayed in a color different from the color of the other nodes.

As described above, the information processing apparatus 11 shown in FIG. 1 has the motif calculating function, the motif displaying function, and the motif details displaying function. These functions may be applied to a protein network to offer the following advantages:

It is possible to easily extract partial structures (various motifs) representing the causal association of the functions taking positive/negative into consideration, between proteins.

It is possible to know the functions of the proteins in greater detail.

It is possible to detect the activities of molecules requisite to treat functions (growth/stasis) that are responsible for cancer, for example, based on the above advantages.

The actions that the user needs to make to obtain the above advantages are simple, and the above various advantages can be obtained in a short time.

The present invention as described above is applied to the detection/analysis of motifs between three modes of a protein network. However, the present invention is not limited to the above application. The present invention is also applicable to various networks other than a protein network, and to the detection/analysis of motifs between n nodes (n represents an integer of 3 or more) in various networks including a protein network.

For example, in a protein network, two edge attributes, i.e., P and N, are assigned as node attributes. However, three or more attributes may be assigned to nodes depending on the type of a network. MotifID of motifs representing the connected relationship between three nodes of such a network may be as follows: Or stated otherwise, steps S3a-M through S3d-M, to be described below, may be performed to calculate MotifID in step S3 shown in FIG. 3.

For example, according to a network wherein a certain node has m properties (m is an integer of 2 or more) depending on how the node is connected to other nodes, the m properties may be employed as node attributes.

In step S3a-M, the processor 31 converts assigned attributes of the m attributes per each of "in", "out" into numerical values according to an (m+1)-ary notation of 1, . . . , m, in the relationship of each of the three nodes making motifs to another node connected thereto. Then, the processor 31 produces numerical values calculated as {in_num*(m+1)-out_num} where in_num, out_num represent (m+1)-ary representations of "in", "out", as link numerical values.

Subsequently, steps S3b-M through S3d-M are performed in the same manner as steps S3b through S3d described above with respect to the protein network.

For detecting/analyzing motifs representing the connected relationship between n nodes of a protein network, MotifID may be as follows: Or stated otherwise, steps S3a-N through S3d-N, to be described below, may be performed to calculate MotifID in step S3 shown in FIG. 3.

Since positions v1, v2, . . . , vn are present for nodes, the processor 31 produces node link numerical values with respect to each of the nodes at the positions v1, v2, . . . , vn in steps S3a-N, S3b-N.

In step S3c-N, the processor 31 produces a numerical sequence of the node link numerical values of the nodes at the positions v1, v2, . . . , vn in a predetermined order, e.g., in the order named in the present embodiment, the numerical sequence being represented by MotifID(original). Specifically, if the node link numerical values of the nodes at the positions v1, v2, . . . , vn are represented by v1_node_num, v2_node_num, . . . , vn_node_num, respectively, then the numerical sequence (v1_node_num v2_node_num . . . vn_node_num) is represented by MotifID(original).

In step S3d-N, the processor 31 produces a numerical sequence made up of the node link numerical values of the nodes at the positions v1, v2, . . . , vn where the node link numerical values are arranged in ascending order, the numerical sequence being represented by MotifID(unique).

Furthermore, for detecting/analyzing motifs representing the connected relationship between n nodes of a network of nodes having m attributes, MotifID may be as follows: Or stated otherwise, steps S3a-NM through S3d-NM, to be described below, may be performed to calculate MotifID in step S3 shown in FIG. 3.

Steps S3a-NM, S3b-NM may be a combination of steps S3a-M, S3b-M and steps S3aN, S3bN described above. Specifically, in steps S3a-NM, S3b-NM, attributes of "in", "out" are expressed by (m+1)-ary representations with respect to each of the nodes at the positions v1, v2, . . . , vn, and numerical values according to {in*(m+1)+out} are produced as link numerical values.

Thereafter, steps S3c-NM, S3d-NM are performed in the same manner as steps S3c-N, S3d-N described above to generate MotifID(original) and MotifID(unique).

By employing MotifID(original) and MotifID(unique) thus generated, steps S4, S5 shown in FIG. 3 can be carried out similarly, and the motif displaying process shown in FIG. 7 and the motif details displaying processes shown in FIGS. 9, 11, and 12 can also can be carried out similarly. However, motifs between n nodes are processed with respect to the n nodes, rather than the three nodes.

The above processing sequence can be implemented by either hardware or software.

Figure 14:
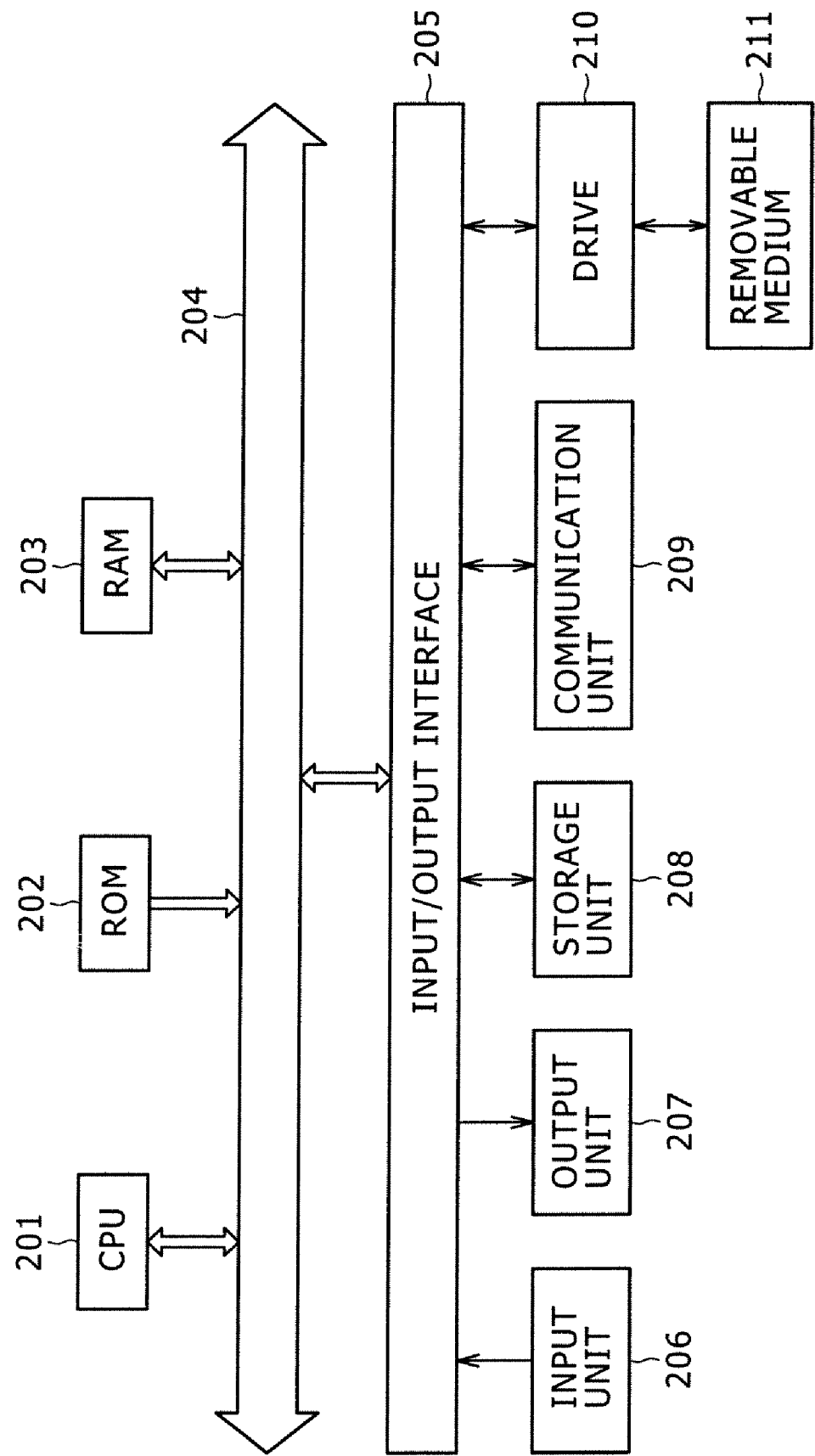
FIG. 14 is a block diagram of a structure of a computer which may be programmed to carry out an information processing method according to an embodiment of the present invention.

At least a portion of the information processing apparatus 11 shown in FIG. 1 may include a personal computer shown in FIG. 14, for example.

In FIG. 14, a CPU (Central Processing Unit) 201 executes various processes according to a program stored in a ROM (Read Only Memory) 202 or a program loaded from a storage unit 208 into a RAM (Random Access Memory) 203. The RAM 203 also stores data requisite for the CPU 201 to perform the various processes.

The CPU 201, the ROM 202, and the RAM 203 are connected to each other through a bus 204. An input/output interface 205 is also connected to the bus 194.

To the input/output interface 205, there are connected an input unit 206 including a keyboard, mouse, etc., an output unit 207 including a display, etc., the storage unit 208 including a hard disk or the like, and a communication unit 209 including a modem, a terminal adapter, or the like. The communication unit 209 controls communications with another device, not shown, through a network including the Internet.

If necessary, a drive 210 is also connected to the input/output interface 205. When a removable medium 211 such as a magnetic disk, an optical disk, a magneto-optical disk, or a semiconductor memory is inserted into the drive 210, the drive 210 reads a computer program from the removable medium 211 and installs the computer program in the storage unit 208 when necessary.

If the processing sequence is implemented by software, the program of the software is installed from a network or a recording medium into a computer incorporated in dedicated hardware or a general-purpose computer which is capable of performing various functions with various programs installed therein.

As shown in FIG. 14, the recording medium which stores programs installed in the computer and executable by the computer includes the removable medium 211 as a package medium such as a magnetic disk (including a flexible disk), an optical disk (including a CD-ROM (Compact Disc-Read Only Memory) and a DVD (Digital Versatile Disc)), a magneto-optical disk (including an MD (Mini-Disk)), or a semiconductor memory, which may be distributed to provide the programs to the user separately from the apparatus itself, the ROM 202 which stores programs and is provided to the user as being incorporated in the apparatus itself, or a hard disk included in the storage unit 208.

In the present specification, steps of describing a program to be stored in the recording medium include processes to be chronologically carried out in the order that is described and processes to be carried out parallel to each other or individually rather than chronologically.

In the present specification, the system refers to an overall arrangement made up of a plurality of apparatus and processors. Stated otherwise, the information processing apparatus 11 and the database 12 shown in FIG. 1 are combined into a system.

Although certain preferred embodiments of the present invention have been shown and described in detail, it should be understood that various changes and modifications may be made therein without departing from the scope of the appended claims.

What is claimed is:

1. An apparatus for processing information about a network including a plurality of nodes, wherein m attributes (m represents an integer of 2 or more) assignable to each of said nodes are defined depending on the relationship to another node which can be connected to said each of the nodes, said apparatus comprising:
   identifier generating means for converting attributes assigned to each of n nodes (n represents an integer of 3 or more) per relationship to the other node connected thereto into numerical values with respect to motifs extracted from said network as predetermined patterns of the connected relationship of the n nodes, and generating identifiers identifying said motifs using said numerical values; and
   analyzing means for determining at least one of said motifs included in said network as an object to be analyzed based on said identifiers generated by said identifier generating means, performing a predetermined analyzing process on said object to be analyzed, and calculating the number of occurrences in said network of a corresponding motif with respect to each of said identifiers generated by said identifier generating means according to said analyzing process.

2. The apparatus according to claim 1, further comprising:
   presenting means for presenting said number of occurrences and information about the corresponding motif with respect to each of said identifiers generated by said identifier generating means.

3. The apparatus according to claim 2, wherein said presenting means further presents information about a predetermined one of said n nodes included in the corresponding motif with respect to said each of the identifiers generated by said identifier generating means.

4. The apparatus according to claim 2, wherein said analyzing means retrieves one or more identifiers corresponding to one or more motifs including a predetermined node from the identifiers generated by said identifier generating means, and said presenting means further presents information about each of said one or more motifs corresponding to said one or more identifiers retrieved by said analyzing means.

5. A method of processing information in an apparatus for processing information about a network including a plurality of nodes, wherein m attributes (m represents an integer of 2 or more) assignable to each of said nodes are defined depending on the relationship to another node which can be connected to said each of the nodes, said method comprising the steps of:
   converting attributes assigned to each of n nodes (n represents an integer of 3 or more) per relationship to the other node connected thereto into numerical values with respect to motifs extracted from said network as predetermined patterns of the connected relationship of the n nodes;
   generating identifiers identifying said motifs using said numerical values;
   determining at least one of said motifs included in said network as an object to be analyzed based on said identifiers;
   performing a predetermined analyzing process on said object to be analyzed, and
   calculating the number of occurrences in said network of a corresponding motif with respect to each of said identifiers according to said analyzing process.

6. A program for enabling a computer to control processing information about a network including a plurality of nodes, wherein m attributes (m represents an integer of 2 or more) assignable to each of said nodes are defined depending on the relationship to another node which can be connected to said each of the nodes, said program comprising the steps of:
   converting attributes assigned to each of n nodes (n represents an integer of 3 or more) per relationship to the other node connected thereto into numerical values with respect to motifs extracted from said network as predetermined patterns of the connected relationship of the n nodes;
   generating identifiers identifying said motifs using said numerical values;
   determining at least one of said motifs included in said network as an object to be analyzed based on said identifiers;
   performing a predetermined analyzing process on said object to be analyzed, and
   calculating the number of occurrences in said network of a corresponding motif with respect to each of said identifiers according to said analyzing process.

7. An apparatus for processing information about a network including a plurality of nodes, wherein m attributes (m represents an integer of 2 or more) assignable to each of said nodes are defined depending on the relationship to another node which can be connected to said each of the nodes, said apparatus comprising:
   an identifier generating section configured to convert attributes assigned to each of n nodes (n represents an integer of 3 or more) per relationship to the other node connected thereto into numerical values with respect to motifs extracted from said network as predetermined patterns of the connected relationship of the n nodes, and generate identifiers identifying said motifs using said numerical values; and
   an analyzing section configured to determine at least one of said motifs included in said network as an object to be analyzed based on said identifier generated by said identifier generating section, perform a predetermined analyzing process on said object to be analyzed, and calculate the number of occurrences in said network of a corresponding motif with respect to each of said identifiers generated by said identifier generating section according to said analyzing process.

* * * * *